United States Patent [19]

Wolters et al.

[11] 3,987,101

[45] Oct. 19, 1976

[54] PROCESS FOR PREPARING CYCLOALKANONES AND CYCLOALKANOLS

[75] Inventors: Jan Wolters, Sittard; Jan L. J. P. Hennekens, Geleen, both of Netherlands

[73] Assignee: Stamicarbon B.V., Geleen, Netherlands

[22] Filed: Oct. 19, 1973

[21] Appl. No.: 408,048

[30] Foreign Application Priority Data

Oct. 9, 1973 Netherlands .................... 7313829

[52] U.S. Cl. .................... 260/586 R; 260/617 C; 260/631 R

[51] Int. Cl.² .................. C07C 45/00; C07C 29/00; C07C 27/04

[58] Field of Search ........ 260/586 R, 586 B, 631 R, 260/610 B, 621 C, 586 P, 617 C

[56] References Cited
UNITED STATES PATENTS

| | | | |
|---|---|---|---|
| 2,497,349 | 2/1950 | Farkas et al. .................... | 260/610 B |
| 2,851,496 | 9/1958 | Cates et al. .................... | 260/631 R |
| 3,187,052 | 6/1965 | Nelson et al. .................... | 260/621 C |

FOREIGN PATENTS OR APPLICATIONS

| | | | |
|---|---|---|---|
| 2,061,113 | 6/1971 | Germany .................... | 260/586 R |

OTHER PUBLICATIONS

Berkman et al., "Catalysis, Inorg. and Org.," pp. 274–276, (1940).

*Primary Examiner*—Norman Morgenstern
*Attorney, Agent, or Firm*—Cushman, Darby & Cushman

[57] ABSTRACT

A process for preparing cycloalkanones and cycloalkanols by conversion of cycloalkylhydroperoxides under the influence of a solid heterogeneous catalyst wherein cycloalkylhydroperoxides having 5–12 carbon atoms in the ring are converted under the influence of an oxidic, chromium catalyst which does not contain any copper oxide.

8 Claims, No Drawings

PROCESS FOR PREPARING CYCLOALKANONES AND CYCLOALKANOLS

The invention relates to a process for preparing cycloalkanones and cycloalkanols by conversion of cycloalkylhydroperoxides under the influence of a solid heterogeneous catalyst.

A process of this type is known from Kogyo Kagaku Zasshi 73 (1970), 2056–8. From this article appears that cyclohexylhydroperoxide can be converted in cyclohexane solution under the influence of some metal-oxides and -sulfides. Amongst the oxides and sulfides examined, some were active as a catalyst for the conversion of cyclohexylhydroperoxide into cyclohexanol and cyclohexanone and others were not.

In the preparation of cycloalkanones and cycloalkanols from cycloalkylhydroperoxides it is of importance to work at a temperature at which the non-catalyzed, thermal decomposition of the cycloalkylhydroperoxide makes as little as possible a contribution to the total conversion of the cycloalkylhydroperoxide and the catalyzed conversion as large as possible a contribution. For, in comparison with the catalyzed conversion, the thermal decomposition of the peroxide is little specific in the direction of the desired products, cycloalkanone and cycloalkanol. In the thermal decomposition a relatively large amount of undesirable by-product is formed. At temperatures of over about 120° C the thermal decomposition of the peroxide proceeds at a clearly perceptible rate. In this respect, therefore, it is desirable to work at a temperature of below approximately 120° C. Below 80° C the speed of the thermal decomposition reaction is so small as to be negligible.

The periodical-article mentioned does not indicate any catalysts with the aid of which this object could be reasonably achieved. It is mentioned that at 70° C cobalt(III)oxide is not active at all, and that molybdenum sulfide is only active if present in a large quantity and even then to only a small degree. Temperatures of 120° C and higher are necessary to be able to cause the conversion desired to proceed at a satisfactory rate. This leads to a decrease in efficiency.

From the U.S. Patent Specification No. 2,851,496 a process is known for the preparation of cyclohexanone and cyclohexanol, in which in a first step cyclohexane in the liquid phase is oxidized with air in the presence of a homogeneous catalyst, like cobaltnaphthenate, and, in a second step, the reaction mixture of the first step is passed over a heterogeneous catalyst, for instance cobalt(II)oxide, vanadium oxide-on-aluminium oxide, molybdenum sulfide or cobalt oxide-on-charcoal, at a temperature of, for instance, 70° C. The reaction mixture of the first step contains cyclohexylhydroperoxide, which is converted for the larger part into cyclohexanone and cyclohexanol in the second step. The quantity of heterogeneous catalyst used is not indicated.

From experiments conducted by Applicant however it has appeared that a very large amount of catalyst is needed in order to achieve a satisfactory conversion rate with the catalysts known from said U.S. Patent Specification, and, hence, the catalyst costs of this known process are high. This holds, a fortiori, if the catalysts containing noble metal are used which are also mentioned in said Patent Specification.

In the non-prepublished Netherlands Patent Application No. 72,14299 of Applicant the use is described of copper-chromium-oxide as a catalyst for conversion of cycloalkylhydroperoxides into cycloalkanones and cycloalkanols.

According to the invention cycloalkanones and cycloalkanols are prepared by converting cycloalkylhydroperoxides with 5–12 carbon atoms in the ring under the influence of an oxidic chromium catalyst, which does not contain any copper oxide. Metals other than copper and chromium may be present.

With application of the catalysts according to the invention extremely high conversion rates of cycloalkylhydroperoxides into cycloalkanones and cycloalkanols can be reached already at low temperatures, for instance temperatures of between 60° and 110° C. The specific conversion rate (s.c.r.), expressed in moles of cycloalkylhydroperoxide converted per kg of heterogeneous catalyst per hour at 80° C, may be extremely high, for instance in the order of 100–1000 or even higher. This number can be compared with the number for molybdenum sulfide at 70° C, viz. 10, calculated on the basis of the data contained in the quoted article from Kogyo Kagaku Zasshi.

The selectivity of the conversion according to the invention into the desired products cycloalkanone and cycloalkanol is high and amounts to 95–100 %, referred to converted peroxide. This means that 0–5 % of the peroxide is converted into by-products. If working in cycloalkane as a solvent, which cycloalkane corresponds with the cycloalkylhydroperoxide, one sometimes finds a yield of more than 100 %. This phenomenon is brought about by oxidation of some solvent with the peroxide. Also in this case at most 5 % of the peroxide plus the converted cycloalkane are converted into by-products.

A matter of importance in the preparation of cycloalkanones and cycloalkanols from cycloalkylhydroperoxides is the ratio in which the ketone and the alcohol are obtained. For most applications preference is given to the cycloalkanone over the cycloalkanol. From experiments carried out by Applicant has appeared that the alcohol to ketone ratio in the reaction product of the decomposition of cyclohexylhydroperoxide at 80° C in cyclohexane as a solvent with one of the known catalysts cobalt(II)oxide, vanadium oxide or platinum lies between 1.1 and 2.4. In the case of the catalysts according to the invention said ratio is more favourable, as a rule below 0.5. Even an alcohol to ketone ratio of less than 0.1 can be obtained.

The catalysts applied in the process according to the invention may or may not be supported on a carrier. Suitable carrier materials are silica, alumina, titanium dioxide, molecular sieves, magnesium oxide, tin dioxide, carbon, and the like.

Application of various modified types of the carrier materials is possible. For instance, both the microporous and the macroporous varieties may be applied. Highly suitable silica carrier materials are, amongst others, 'Aerosil' (Degussa trade-mark) and 'Ketjensil' (AKZO trade-mark). The catalyst particles may have different shapes, for instance the spherical, the saddle or the tablet shape. Preferably, a solid catalyst bed is applied, but the catalyst may also be present as a suspension, in a finely divided form, in the reaction mixture.

The catalyst preparation process has a considerable influence on the specific rate of conversion. By preference, chromium oxide obtained by heating a suitable chromium compound, like chromium(III)hydroxide, is applied as catalyst. It is of advantage that, prior to being used, the catalyst is activated by heating at 300°–500° C in an atmosphere of a gas containing molecular oxygen, for instance air. Particularly high specific conversion rates are obtainable with catalysts prepared according to the method described in Applicant's Netherlands Patent Application No. 6705259 which has been laid out for inspection.

With catalysts supported on carriers also the degree to which the carrier is loaded with catalytically active material is of importance. Preferably, a low load factor, for instance of at most 10 % by weight of Cr, is applied. A catalyst of this kind appears to be highly active, compared with catalysts with a high load factor, and to retain its activity also for a long period.

The chromium in the catalyst may be of different valencies, for instance trivalent and hexavalent. Surprisingly, it has been found that a very active and long-lived catalyst, in which the chromium is principally present as chromium(VI)oxide, can be obtained by heating chromium(III)oxide at 300°–500° C in an atmosphere of a gas containing molecular oxygen, for instance air. Also a chromium compound may be started from which when heated changes into chromium(III)oxide, for instance chromium(III)hydroxide. A practically complete transition from chromium(III) to chromium(VI) is achieved with catalysts having a low load factor, particularly those which appear amorpheus in X-raying.

It is noted that the preparation of mixtures of ketones and the corresponding alcohols by treatment of a solution of a secondary hydroperoxide in an organic solvent with an aqueous solution of $CrO_3$ which is not miscible with the organic phase is known from the Netherlands Patent Application No. 7017769. This known process results in a low efficiency and a high catalyst consumption. The process according to the invention on the other hand does not involve these disadvantages and, moreover, is technically realizable with substantially more simplicity.

The process for preparing cycloalkanones and cycloalkanols according to the invention is by preference carried out at a temperature of between 30° and 150° C. At temperatures lower than 30° C the conversion rate is insufficiently large. For reasons already mentioned above, usually a lower efficiency in desired products is obtained at temperatures above 120° C, unless an exceptionally active catalyst system is applied. The 60°–100° C temperature range constitutes a proper compromise between a small reaction speed at a low temperature and a small selectivity at a high temperature.

The reaction pressure is not critical. Generally, the reaction is carried out with a solution of the cycloalkylhydroperoxide in a liquid distributing agent, so that it will then become necessary to apply a pressure at which a liquid phase is maintained in the system. For technical reasons, a pressure of 1 atmosphere or slightly higher is preferred, although also lower and higher pressures, for instance of 0.1–20 atmospheres, may be applied, dependent on the distributing agent and the cycloalkylhydroperoxide used. The peroxide concentration as a rule amounts to 2–20 % by weight.

As distributing agents are to be considered distributing agents that are inert under the reaction conditions, as well as the cycloalkane which corresponds with the cycloalkylhydroperoxide used. Said cycloalkane is given preference because in this case more than one molecule of cycloalkanone or cycloalkanol can form to every molecule of cycloalkylhydroperoxide applied. Examples of suitable inert distributing agents are aromatic hydrocarbons, like benzene. The water set free during the reaction may be discharged in a suitable way as an azeotrope with the distributing agent.

The cycloalkylhydroperoxide may be prepared by oxidation of the corresponding cycloalkane in the liquid phase at elevated temperature with an oxygen-containing gas, such as air. Low conversions on the basis of cycloalkane supplied, for instance 1–12 % are worked at. Suitable oxidation temperatures lie between 140° and 180° C. The operating pressure is not critical but should be such that a liquid phase is maintained in the system. Usually, the pressure lies between 4 and 50 atmospheres.

By preference, the oxidation reaction is carried out in the absence of substances which promote the decomposition of cycloalkylhydroperoxide, like compounds of transition metals. In order to achieve this object reactors having an inert internal wall, for instance of passivated steel, aluminium, tantalum, glass, enamel and the like, may be applied. In this way the aspecific decomposition of the cycloalkylhydroperoxide at the oxidation temperature which is generally relatively high is avoided as much as possible.

The oxidation reaction yields a hot, rather dilute solution of cycloalkylhydroperoxide in cycloalkane, which solution is under pressure. It is appropriate for the resulting solution to be subsequently expanded to a lower pressure, for instance to approximately 1 atmosphere. If the cycloalkane should be cyclopentane, cyclohexane or cycloheptane, such an amount of cycloalkane will evaporate during said expansion that the temperature drops to 60°–100° C, which is a highly suitable temperature range for the conversion according to the invention, so that the concentrated solution obtained, which contains cycloalkylhydroperoxide, can be subjected to the process according to the invention without further measures. However, it would serve a good purpose for the crude solution to be stripped, at least partly, from any contaminants, for instance by washing it with water. In this way fouling of the catalyst is opposed. It is also possible first to separate off pure cycloalkylhydroperoxide from the oxidation product mixture, for instance by extraction with an aqueous alkaline solution, followed by acidulation and further processing of the extract, and to use the pure peroxide as a starting material.

The process according to the invention is suitable for both batchwise and continuous operation.

The invention will now be elucidated by means of the following examples.

EXAMPLE I

Chromium(III)oxide is heated for a few hours at 300° C, whilst air is being passed over. 250 mg of the chromium(III)oxide pre-treated is this way are added to 35 ml of a 0.14 molar solution of cyclohexylhydroperoxide in cyclohexane, and the mixture is rapidly given a temperature of 80° C.

After 60 minutes of stirring, 33 % of the hydroperoxide is converted into cyclohexanone, and, besides, into a small quantity of cyclohexanol. The alcohol to ketone ratio amounts to 0.07.

EXAMPLE II 100 g of silica (Aerosil, Degussa trade-mark) are suspended in 1.5 liters of water, 194.5 g of $Cr(NO_3)_3 \cdot 9 H_2O$ and 87.6 g of urea are added. The reaction mixture is heated to 95° C, with stirring, and kept at this temperature for 17 hours.

The solid is filtered off and washed out with hot distilled water, and subsequently dried at 120° C and compressed to form 3 mm dia tablets. The catalyst obtained is calcined in air for 1 hour at 450° C.

A catalyst is obtained having a chromium content of 26.2 %.

140 mg of the catalyst so prepared are suspended in 25 ml of cyclohexane, and a solution of 490 mg of cyclohexylhydroperoxide in 10 ml of cyclohexane is added to said suspension. The resulting mixture is rapidly heated to 80° C. After 2 minutes of stirring, with reflux, the conversion of the hydroperoxide amounts to 98 %. The specific conversion rate amounts to 3400 moles of hydroperoxide converted per kg of Cr per hour. The yields in cyclohexanol and cyclohexanone amount to 105 % referred to the hydroperoxide applied, whilst the ratio between the cyclohexanol formed and the cyclohexanone formed amounts to 0.43.

EXAMPLE III

An oxidation mixture is prepared by oxidizing cyclohexane in the liquid phase with air in the absence of a catalyst and by concentrating the resulting reaction mixture by evaporation until a cyclohexylhydroperoxide content of approximately 700 mmoles/kg is obtained.

At 70° C, said mixture is passed over a catalyst bed consisting of chromium(III)oxide on alumina (Alosil of Messrs Degussa) in the form of tablets. The chromium content of the catalyst amounts to 35.6 % by weight.

At a residence time of 2 minutes, the conversion of cyclohexylhydroperoxide amounts to 45 %. Cyclohexanol and cyclohexanone are formed in a ratio of 0.44 and at a yield of 99 %, referred to converted cyclohexylhydroperoxide.

EXAMPLE IV

The procedure is analogous to the method of example III, now with tablets of a catalyst consisting of 34.5 % by weight of chromium(III)oxide on titanium oxide (Titosil of Messrs. Degussa). An oxidation mixture is started from containing 700 mmoles/kg of cyclohexylhydroperoxide, 39 % of the hydroperoxide is converted, with a yield of 98 % in cyclohexanone and cyclohexanol formed.

EXAMPLE V

An oxidation mixture obtained by oxidation of cyclohexane in the liquid phase with air is concentrated by evaporation, whereupon the cyclohexylhydroperoxide content amounts to 0.591 mol/kg. This mixture is passed through a column at 70° C from the bottom upwards, which column is filled with tablets consisting of chromium(III)oxide on Aerosil. This catalyst has been prepared in accordance with the description of Example II and it contains 26.2 % by weight of chromium. At a residence time of 1 minute the conversion of cyclohexylhydroperoxide into a mixture of cyclohexanone and cyclohexanol amounts to 48 %. Cyclohexanol and cyclohexanone are formed in a ratio of 0.43 and with a yield of 102 %, referred to converted cyclohexylhydroperoxide.

EXAMPLE VI 450 g of silicon dioxide (Ketjensil; marketed by AKZO) are suspended in 6 liters of water. 131.6 g of $Cr(NO_3)_3 \cdot 9 H_2O$ and 59.2 g of urea are added. The reaction mixture is heated to 99° C, with stirring and kept at this temperature for 21 hours. The solid is filtered off and washed out with cold distilled water, whereupon it is dried at 120° C for 16 hours. The green-coloured mass is now calcined in air at 420° C for 1 hour, during which the colour changes to yellow.

The catalyst obtained, which is amorphous in X-raying, contains 3.1 % by weight of chromium, which appears to be present in the form of $CrO_3$. The catalyst is compressed to form tablets having a diameter of 5 mm.

Through oxidation of cyclohexane in the liquid phase with air as oxidizing agent, followed by concentration by evaporation and washing of the resulting mixture with water, an oxidation mixture is obtained which, by the side of cyclohexane, contains 698 mmoles/kg of cyclohexylhydroperoxide, 172 mmoles/kg of cyclohexanol and 155 mmoles/kg of cyclohexanone.

This mixture is passed through a vertically arranged column at a rate of about 250 ml per hour, in which column there are tablets of the above catalyst obtained.

The column is kept at 100° C. The pressure amounts to 3.4 atm. At a contact time of 2.5 minutes of the reaction mixture and the catalyst the conversion amounts to 72 %.

In an experiment according to this example, with the aid of 8 g of the catalyst, 28 moles of cyclohexylhydroperoxide were converted into cyclohexanol and cyclohexanone with a yield of 97.4 %, the specific conversion rate being practically constant.

We claim:

1. A process for preparing cycloalkanones and cycloalkanols by conversion of cycloalkylhydroperoxides under the influence of a solid heterogeneous catalyst comprising converting a cycloalkylhydroperoxide having 5–12 carbon atoms in the ring by heating said cycloalkylhydroperoxide at a temperature of from about 30° C to about 150° C in the presence of a copper oxide-free chromium oxide catalyst wherein the valency of the chromium is from 3 to 6.

2. Process according to claim 1, characterized in that the conversion of cycloalkylhydroperoxide is carried out at a temperature of between 60° and 110° C.

3. A process according to claim 1 wherein said catalyst is produced from a compound decomposable into chromium oxide when heated.

4. A process according to claim 1 wherein said catalyst is supported on a carrier with a load factor of not more than 10% by weight of chromium.

5. A process according to claim 1 wherein the catalyst is chromium (VI) oxide.

6. A process according to claim 4, wherein said catalyst is prepared by heating at 300°–500° C in the presence of a molecular oxygen containing gas a chromium (III) oxide or a compound changeable thereto upon heating.

7. The process of claim 1 wherein the cycloalkylhydroperoxide used is employed as a solution in the corresponding cycloalkane derived from the liquid phase oxidation of the cycloalkane using a molecular oxygen containing gas as the oxidant.

8. The process of claim 7 wherein the liquid phase oxidation reaction product is washed with water prior to use in the conversion process.

* * * * *